US00PP16865P2

(12) United States Plant Patent
Vester

(10) Patent No.: US PP16,865 P2
(45) Date of Patent: Jul. 25, 2006

(54) ***PHLOX* PLANT NAMED 'JUNIOR BOUQUET'**

(50) Latin Name: *Phlox paniculata*
Varietal Denomination: Junior Bouquet

(75) Inventor: Mart Vester, Zwaanshoek (NL)

(73) Assignee: Green Works International B.V., 't Zand (NL)

( * ) Notice: Subject to any disclaimer, the term of this patent is extended or adjusted under 35 U.S.C. 154(b) by 155 days.

(21) Appl. No.: 10/878,565

(22) Filed: Jun. 28, 2004

(51) Int. Cl.
*A01H 5/00* (2006.01)

(52) U.S. Cl. ..... Plt./320

(58) Field of Classification Search ..... Plt./320
See application file for complete search history.

*Primary Examiner*—Anne Marie Grunberg
(74) *Attorney, Agent, or Firm*—C. A. Whealy

(57) ABSTRACT

A new and distinct cultivar of *Phlox* plant named 'Junior Bouquet', characterized by its upright and compact plant habit; freely basally branching habit and short internodes; dense and bushy growth habit; attractive dark pink-colored flowers with red purple-colored centers; freely and continuous flowering habit; resistance to Powdery Mildew; and good garden performance.

2 Drawing Sheets

Botanical classification/cultivar designation: *Phlox paniculata* cultivar Junior Bouquet.

BACKGROUND OF THE INVENTION

The present Invention relates to a new and distinct cultivar of *Phlox* plant, botanically known as *Phlox paniculata,* and hereinafter referred to by the cultivar name Junior Bouquet.

The new *Phlox* is a product of a planned breeding program conducted by the Inventor in Zwaanshoek, The Netherlands. The objective of the breeding program was to create new compact *Phlox* cultivars with attractive flower coloration and resistance to Powdery Mildew.

The new *Phlox* originated from a cross-pollination made by the Inventor in 1996 in Zwaanshoek, The Netherlands of a proprietary selection of *Phlox paniculata* identified as code number 95.05.28, not patented, as the female, or seed, parent with a proprietary selection of *Phlox paniculata* identified as code number 95.05.07, not patented, as the male, or pollen, parent. The new *Phlox* was discovered and selected by the Inventor as a flowering plant within the progeny of the stated cross-pollination in a controlled environment in Zwaanshoek, The Netherlands in 1998.

Asexual reproduction of the new cultivar by terminal cuttings at Zwaanshoek, The Netherlands since 1998, has shown that the unique features of this new *Phlox* are stable and reproduced true to type in successive generations.

SUMMARY OF THE INVENTION

Plants of the cultivar Junior Bouquet have not been observed under all possible environmental conditions. The phenotype may vary somewhat with variations in environment such as temperature and light level without, however, any variance in genotype.

The following traits have been repeatedly observed and are determined to be the unique characteristics of 'Junior Bouquet'. These characteristics in combination distinguish 'Junior Bouquet' as a new and distinct cultivar of *Phlox.*

1. Upright and compact plant habit.
2. Freely basally branching habit and short internodes; dense and bushy growth habit.
3. Attractive dark pink-colored flowers with red purple-colored centers.
4. Freely and continuous flowering habit.
5. Resistant to Powdery Mildew.
6. Good garden performance.

Plants of the new *Phlox* differ primarily from plants of the parent selections in plant habit as plants of the new *Phlox* are more compact than plants of the parent selections. In addition, plants of the new *Phlox* and the female parent selection differ in flower coloration.

Plants of the new *Phlox* can be compared to the *Phlox paniculata* cultivar Rijnstroom, not patented. In side-by-side comparisons conducted in Zwaanshoek, The Netherlands, plants of the new *Phlox* differed from plants of the cultivar Rijnstroom in the following characteristics:

1. Plants of the new *Phlox* were more compact than plants of the cultivar Rijnstroom.
2. Plants of the new *Phlox* had shorter internodes than plants of the cultivar Rijnstroom.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which more accurately describe the actual colors of the new *Phlox.*

The photograph on the first sheet is a close-up view of a typical inflorescence of 'Junior Bouquet'.

The photograph on the second sheet is a close-up view of a typical flowering branch of 'Junior Bouquet'.

DETAILED BOTANICAL DESCRIPTION

The aforementioned photographs, following observations and measurements describe plants grown in 't Zand, The Netherlands, in an outdoor nursery and under commercial production practices during the summer. Plants were about 13 weeks old when the photographs and description were taken. During the production of the plants, day temperatures ranged from 5 to 20° C. and night temperatures ranged from 2 to 12° C. In the following description, color references are made to The Royal Horticultural Society Colour Chart, 1995 Edition, except where general terms of ordinary dictionary significance are used.

Botanical classification: *Phlox paniculata* cultivar Junior Bouquet.

Parentage:

*Female parent.*—Proprietary selection of *Phlox paniculata* identified as code number 95.05.28, not patented.

*Male parent.*—Proprietary selection of *Phlox paniculata* identified as code number 95.05.07, not patented.

Propagation:

*Type.*—By terminal cuttings.

*Time to initiate roots, summer.*—About three weeks at 18° C.

*Time to initiate roots, winter.*—About five weeks at 18° C.

*Time to produce a rooted plant, summer.*—About four weeks at 18° C.

*Time to produce a rooted plant, winter.*—About six weeks at 18° C.

*Root description.*—Thick, well-branched.

Plant description:

*Plant form/habit.*—Upright and compact plant habit; inverted triangle; moderately vigorous growth habit. Freely basally branching habit with short internodes, dense and bushy growth habit.

*Plant height.*—About 65 cm.

*Plant width* (*spread*).—About 35 cm.

*Lateral branches.*—Length: About 65 cm. Diameter: About 3 mm. Internode length: About 2.5 cm. Strength: Strong. Texture: Glabrous. Color: 144B with longitudinal streaks, 159C; at nodes, 79B.

*Foliage description.*—Arrangement: Alternate, simple. Length, lower leaves: About 17.5 cm. Width, lower leaves: About 6 cm. Length, upper leaves: About 9 cm. Width, upper leaves: About 3.5 cm. Shape: Oblanceolate. Apex: Acuminate. Base: Obtuse to attenuate. Margin: Entire. Texture, upper and lower surfaces: Leathery, thick; glabrous. Venation pattern: Pinnate. Color: Developing leaves, upper and lower surfaces: 137B. Fully expanded leaves, upper and lower surfaces: 138B. Venation, upper surface: 137B. Venation, lower surface: 142C. Petiole: Length: About 2 mm. Diameter: About 2 mm. Texture, upper and lower surfaces: Glabrous. Color, upper and lower surfaces: 142C.

Flower description:

*Flower type/habit.*—Single, rounded salverform flowers arranged in terminal panicles; flowers face upright and outward. Panicles conical in shape. Freely flowering habit with about 36 flower buds and flowers per inflorescence.

*Fragrance.*—Faint to moderate; sweet.

*Natural flowering season.*—Continuously flowering from July through September in 't Zand, The Netherlands. Flowers not persistent.

*Postproduction longevity.*—Flowers last about four days on the plant.

*Flower buds.*—Height: About 1.8 cm. Diameter. About 7 mm. Shape: Tubular. Color: 77B to 77C.

*Flowers.*—Diameter: About 2 cm. Depth: About 1.4 cm.

*Petals.*—Quantity per flower: Typically five in a single whorl; petals fused at the base into a narrow tube. Lobe length: About 1.5 cm. Lobe width: About 1 cm. Shape: Obovate to fan-shaped. Apex: Obtuse, rounded to slightly acute. Margin: Entire. Aspect: Mostly flat; margins slightly curved upwards. Texture, upper and lower surfaces: Smooth, glabrous. Color: Developing petals, upper surface: 62A. Developing petals, lower surface: 75B. Fully expanded petals, upper surface: 63B; towards the base, 62B; eye at center of flower, 57B. Fully expanded petals, lower surface: 75B; towards the base, 77B.

*Sepals.*—Quantity per flower: Typically five in a single whorl, fused; narrow tubular calyx. Length: About 5 mm. Width: About 1 mm. Shape: Apiculate. Apex: Acuminate. Texture, upper and lower surfaces: Smooth, glabrous. Color, upper and lower surfaces: Close to 143B.

*Reproductive organs.*—Stamens: Quantity per flower: Typically five; fused with petals in tube. Anther shape: Oblong. Anther length: About 0.5 mm. Anther color: 2D. Pollen amount: Moderate. Pollen color: 2D. Pistils: Quantity per flower: Typically one. Pistil length: About 1 cm. Stigma shape: Bi-parted. Stigma color: 154D. Style length: About 1.4 cm. Style color: 154D. Ovary color: 142C.

*Seed/fruit.*—Seed and fruit development have not been observed.

Disease/pest resistance: Plants of the new *Phlox* have been noted to be resistant to Powdery Mildew. Plants of the new *Phlox* have not been noted to be resistant to other pathogens and pests common to *Phlox*.

Garden performance: Plants of the new *Phlox* have been observed to have good garden performance and tolerate rain, wind and are winter hardy in 'Zand, The Netherlands.

It is claimed:

1. A new and distinct cultivar of *Phlox* plant named 'Junior Bouquet', as illustrated and described.

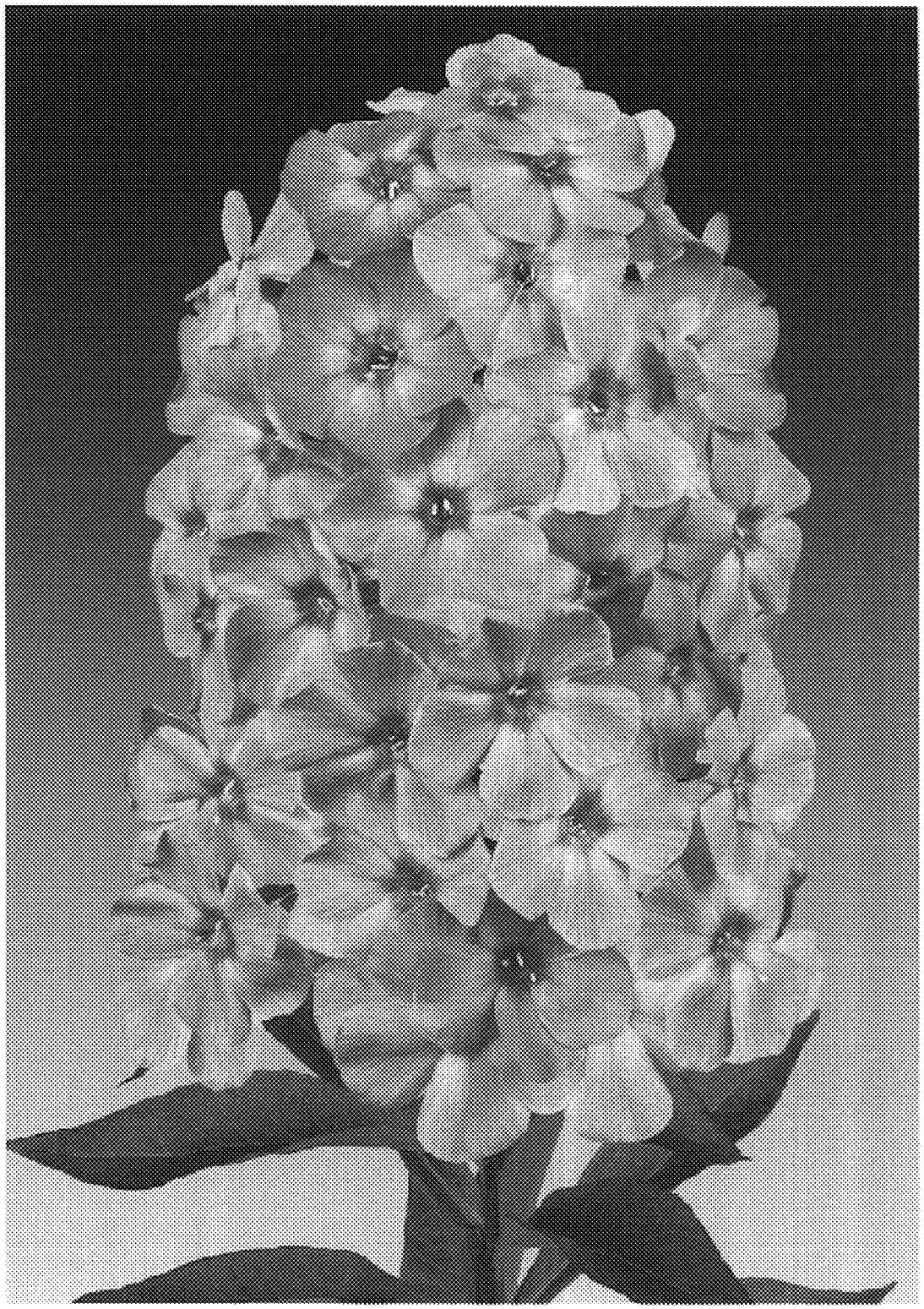

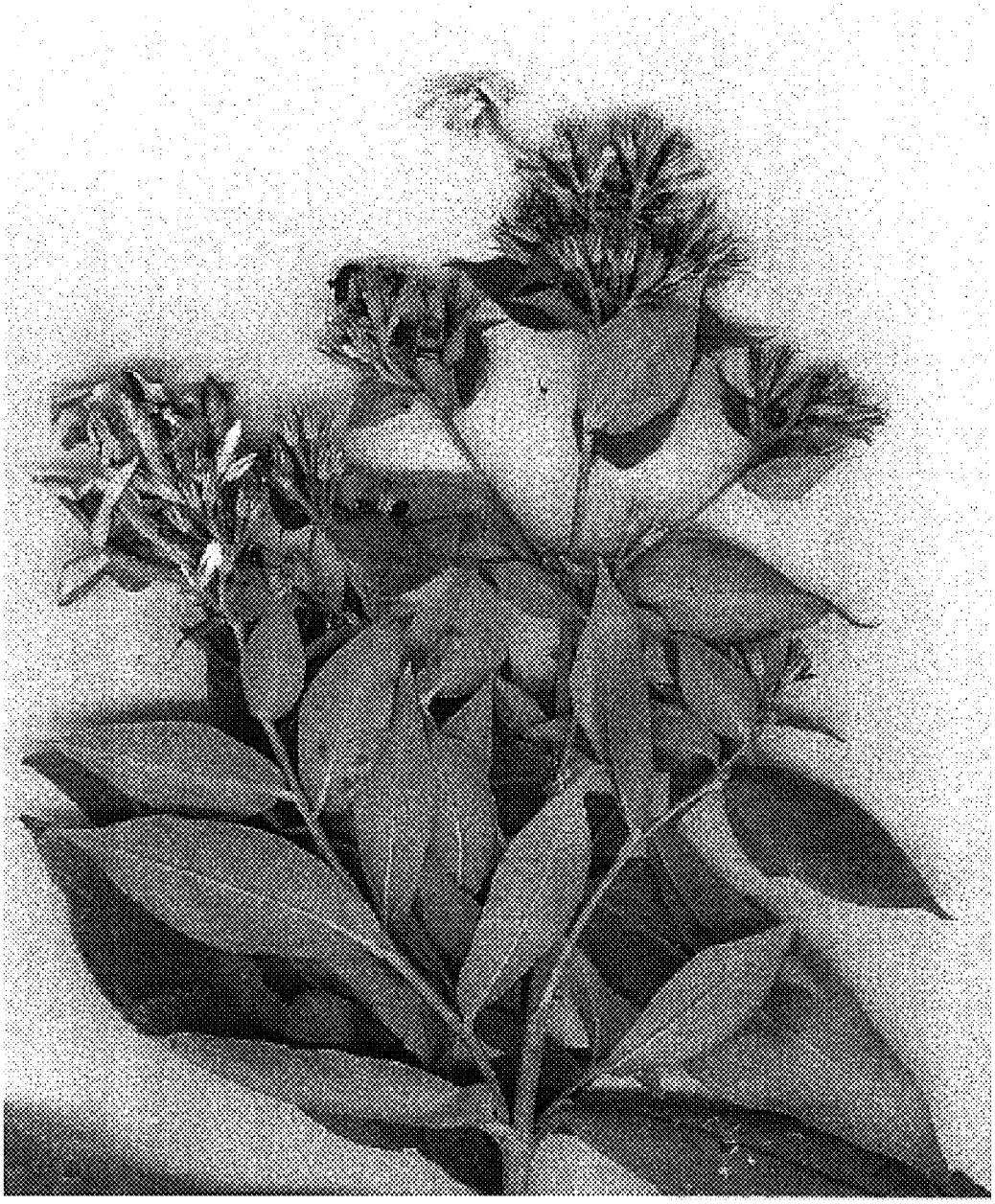

* * * * *